United States Patent [19]

Benoit et al.

[11] Patent Number: 5,380,883

[45] Date of Patent: Jan. 10, 1995

[54] 7-ETHYLENE-α-(METHOXYMETHYLENE)-1-NAPHTHALENE-ACETIC ACID

[75] Inventors: Marc Benoit, Roquevaire; Sylvain Laugraud, Ville D'Avray; Jean-Louis Brayer, Nanteui Le Haudouin, all of France

[73] Assignee: Roussel-Uclaf, France

[21] Appl. No.: 46,555

[22] Filed: Apr. 12, 1993

[30] Foreign Application Priority Data

Apr. 14, 1992 [FR] France .................. 92 04565

[51] Int. Cl.⁶ ............... C07C 69/708; C07F 7/08; A01N 37/36; A01N 55/00
[52] U.S. Cl. .................... 549/438; 549/398; 549/434; 514/532; 514/538; 556/441; 560/10; 560/42; 560/45; 560/56
[58] Field of Search ............ 549/438, 398, 434; 556/441; 560/10, 42, 45, 56; 514/532, 538

[56] References Cited

FOREIGN PATENT DOCUMENTS 0178826 4/1986 European Pat. Off. .
0267734 5/1988 European Pat. Off. .

Primary Examiner—Paul J. Killos
Attorney, Agent, or Firm—Bierman and Muserlian

[57] ABSTRACT

A compound of the formula

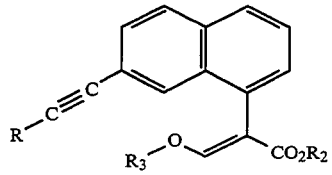

I

19 Claims, No Drawings

7-ETHYLENE-α-(METHOXYMETHYLENE)-1-NAPHTHALENE-ACETIC ACID

OBJECTS OF THE INVENTION

It is an object of the invention to provide the novel compounds of formula I and a process and intermediates for the preparation thereof.

It is another object of the invention to provide parasitic compositions and a novel method of combatting parasites.

These and other objects and advantages of the invention will become obvious from the following detailed description.

THE INVENTION

The novel compounds of the invention have the formula

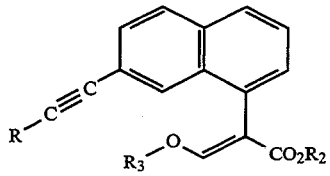

wherein R is selected from the group consisting of A) halogen and hydrogen, B) alkyl, alkenyl, alkynyl and cycloalkyl of up to 8 carbon atoms optionally substituted with at least one member of the group consisting of hydroxy and halogen and optionally interrupted by at least one heteroatom selected from the group consisting of —O—, —S— and nitrogen, C)

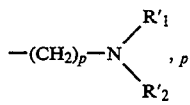

is an integer from 0 to 6, $R'_1$ and $R'_2$ are individually hydrogen or alkyl of 1 to 4 carbon atoms, D) aryl and aryloxy of up to 18 carbon atoms optionally substituted on the aryl by at least one member of the group consisting of halogen, —$NO_2$, —CN, optionally unsaturated alkoxy, alkylthio and cycloalkyl of up to 8 carbon atoms optionally substituted by at least one halogen, aryl and aryloxy of up to 16 carbon atoms optionally substituted by at least one halogen and

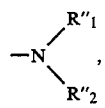

$R''_1$ and $R''_2$ are individually selected from the group consisting of hydrogen, alkyl of 1 to 4 carbon atoms and aryl of up to 18 carbon atoms optionally substituted with at least one halogen, E) aryl and aryloxy of up to 18 carbon atoms optionally substituted on 2 adjacent carbon atoms of the aryl nucleus with methylenedioxy or ethylenedioxy optionally substituted with 1 or 2 halogen atoms, F) heterocyclic aryl of 5 to 6 ring members containing 1 to 3 heteroatoms selected from the group consisting of —O—, —S— and nitrogen and optionally substituted with at least one member of the group consisting of —OH, —$NO_2$, —CN, halogen, alkyl, alkoxy, alkylthio and cycloalkyl of up to 8 carbon atoms optionally substituted by at least halogen and/or hydroxy and

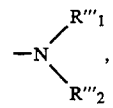

$R'''_1$ and $R'''_2$ are individually hydrogen or alkyl of 1 to 4 carbon atoms,

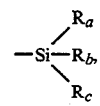

$R_a$, $R_b$ and $R_c$ are individually selected from the group consisting of alkyl and cycloalkyl of up to 4 carbon atoms optionally substituted by at least one halogen, aryl optionally substituted by at least one member of the group consisting of halogen, —OH and alkyl, alkoxy and alkylthio optionally substituted with at least one halogen and H)

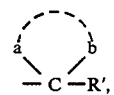

a and b are individually selected from the group consisting of hydrogen, halogen, —OH, alkyl of 1 to 6 carbon atoms optionally substituted by at least one halogen and alkoxy of 1 to 6 carbon atoms or a and b together with the carbon to which they are attached form cycloalkyl of up to 6 carbon atoms, R' has the value of R and $R_2$ and $R_3$ are individually selected from the group consisting alkyl and cycloalkyl of up to 8 carbon atoms optionally substituted by at least one halogen and

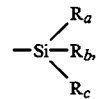

wherein $R_a$, $R_b$ and $R_c$ have the above definitions.

In the compounds of formula I, alkyl may be methyl, ethyl, propyl, isopropyl, butyl, isobutyl, sec-butyl, tert-butyl and cycloalkyl is preferably cyclopropyl, cyclobutyl or cyclopentyl. Unsaturated alkyl is preferably ethenyl, ethynyl, propenyl, propynyl, butenyl or butynyl.

When the alkyl is interrupted by one or more heteroatoms, it is preferably by one or more oxygen or nitrogen atoms. When it is cycloalkyl interrupted by one or more heteroatoms, it is preferably a nitrogenous heterocycle linked by a nitrogen atom such as pyrrolidine, pyrazoline, piperidine, piperazine or morpholine. Aryl is preferably phenyl and heterocyclic aryl is preferably thiazolyl, oxazolyl, isothiazolyl, isoxazolyl, thiadiazolyl, (1,2,4) or (1,3,4) oxadiazolyl, triazolyl, imidazolyl, pyridinyl, pyrimidinyl or pyrazolyl.

If R or R' is halogen, it is preferably bromine or chlorine and if R or R' is a group substituted by a halogen, the halogen is preferably fluorine, chlorine or bromine, $R_2$ is methyl and $R_3$ is methyl preferably.

The geometry of the exo (enol ether) double bond is E or Z and the invention which relates to the E products and the Z products, as well as E+Z mixtures, has more especially the compounds in which the geometry of the exo (enol ether) double bond is E.

Among the preferred compounds of formula I are those wherein R is alkyl of 1 to 6 carbon atoms, preferably tert-butyl or n-butyl, those wherein R is

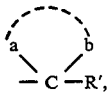

a and b are individually hydrogen, —OH and alkyl of up to 4 carbon atoms or with the carbon atoms to which they are attached form cycloalkyl of up to 4 carbon atoms and R has the above definition. a and b are both hydrogen or methyl or together form cyclopropyl. Other preferred compounds of formula I are those wherein R or R' is

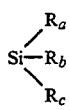

in which $R_a$, $R_b$ and $R_c$ are individually alkyl of up to 4 carbon atoms and especially methyl and those wherein R or R' is phenyl optionally substituted with at least one member of the group consisting of halogen, —OH, alkyl and alkoxy of up to 4 carbon atoms, methylenedioxy, ethylenedioxy and —CF$_3$ and the phenyl is optionally substituted by chlorine, bromine, —CF$_3$, ethoxy or methylenedioxy.

among the preferred compounds of formula I are those of Examples 1 to 4, 15 to 17, 29, 39, 40, 51, 52 and 53.

The pesticidal compositions of the invention are comprised of a pesticidally effective amount of at least one compound of formula I and an inert carrier. The compositions are useful for combatting parasites of vegetation, whether parasites of the soil or of the parts above ground, parasites of premises and parasites of warm-blooded animals.

The compositions can be used to combat parasitic insects, nematodes and acaridae of vegetation and animals and to combat parasites of vegetation, parasites of premises and parasites of warm-blooded animals as well as to combat insects in premises, notably to combat flies, mosquitoes and cockroaches and to combat insects and other parasites of the soil, for example Coleoptera, such as Diabrotica, click beetles and May beetles, Diptera such as cecydomia and Lepidoptera such as owlet moths. They are used at doses comprised between 5 g and 300 g of active ingredient per hectare.

All these properties make the compositions which correspond perfectly to the demands of the modern agrochemical industry and they allow the protection of crops while preserving the environment. The compositions can also be used to combat parasitic acaridae and nematodes of vegetation and are also useful to combat parasitic acaridae of animals, to combat ticks and notably ticks of the Boophilus species, those of the Hyalomnia species, those of the Amblyomnia species and those of the Rhipicephalus species or to combat all sorts of mites and notably the sarcoptic mite, the psoroptic mite and the chorioptic mite.

The compositions are intended to combat parasites of warm-blooded animals, parasites of premises and vegetation and preferably contain at least one of the products of formula I as defined above and especially the products of Example 1 to 4, 15, 16, 17, 29, 39, 40, 51, 52 and 53.

The insecticidal compositions contain as active ingredient at least one of the products defined above and are prepared by the usual processes of agrochemical industry or the veterinary industry or the animal feed products industry.

In the compositions intended for agricultural use and for use in premises, the active ingredient or ingredients can optionally have added to them one or more other pesticide agents. These compositions can be in the form of powders, granules, suspensions, emulsions, solutions, aerosol solutions, combustible strips, baits or other preparations usually employed for the use of this type of compound.

In addition to the active ingredient, these compositions usually contain a vehicle and/or a nonionic surfacant to ensure a uniform dispersion of the constituents of the mixture. The vehicle can be a liquid such as water, alcohol, hydrocarbons or other organic solvents, mineral, animal or vegetable oil, a powder such as talc, clays, silicates or kieselguhr or a combustible solid. The insecticide compositions contain preferably 0.005% to 10% by weight of active ingredient.

According to an advantageous method for use in premises, the compositions of the invention are used in the form of fumigant compositions. The compositions can be advantageously composed of for the non-active part a combustible insecticide coil, or an incombustible fibrous substrate. In the latter case, the fumigant obtained after incorporation of the active ingredient is placed on a heating apparatus such as an electric emanator. When an insecticide coil is used, the inert support can be made of Pyrethrum marc, Tabu powder (or Machilus Thumbergii leaf powder), Pyrethrum stem powder, cedar leaf powder, sawdust (such as pine sawdust), starch and coconut shell powder. The dose of active ingredient can be 0.03% to 1% by weight. In the case where an incombustible fibrous support is used, the dose of active ingredient can be 0.03 to 95% by weight.

The compositions of the invention for use in premises can also be obtained by preparing a sprayable oil based on the active ingredient, this oil soaks a lamp wick and is then set alight. The concentration of active ingredient incorporated in the oil is, preferably, 0.03 to 95% by weight.

The insecticide compositions of the invention as acaricide and nematocide compositions can optionally have at least one other pesticide agent added to them. The acaricide and nematocide compositions can be presented in the form of powders, granules, suspensions, emulsions or solutions.

For acaricide use, wettable powders are preferably used for foliar spraying containing 1 to 80% by weight of active ingredient or liquids for foliar spraying containing 1 to 500 g/l of active ingredient. Powders for foliar dusting containing 0.05% to 3% of active ingredient can also be used. For nematocide use, liquids for soil treatment containing 300 to 500 g/l of active ingredient are preferably used. The acaricide and nematocide compounds of the invention are used preferably at doses of 1 and 100 g of active ingredient per hectare.

To increase the biological activity of the products of the invention, standard synergists used in such cases can be added such as 1-(2,5,8-trioxadodecyl)-2-propyl-4,5-methylenedioxy benzene (or piperonyl butoxide) or N-(2-ethyl-heptyl)-bicyclo-[2.2.1 ]-5-heptene-2,3-dicarboximide, or piperonyl-bis-2-(2'-n-butoxy-ethoxyl) ethylacetal (or tropital).

The compounds of formula I show an excellent general tolerance, and therefore are used to combat illnesses caused by ticks and mites in humans and animals.

The products are notably used to combat lice as a preventative or curative and to combat mites. The products can be administered by external route, by spraying, by shampooing, by bathing or painting on. For veterinary use, the compositions can also be administered by painting the dorsal spine according to the "pour-on" method. It can also be indicated that the compositions can be used as biocides or as growth regulators.

The process of the invention for the preparation of a compound of formula I comprises reacting a compound of the formula

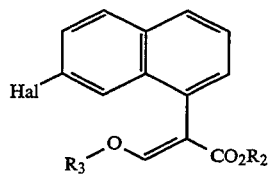  II wherein Hal is halogen and $R_2$ and $R_3$ have the above definitions with a compound of the formula

R—C≡CH    III wherein R has the above definition to obtain the compound of formula I and if R is —OH, optionally reacting it with a functionalization agent. Preferably, the reaction of the compounds of formula II and III is effected in an aprotic dipolar solvent such as acetonitrile in the presence of a tertiary amine such as triethylamine, palladium metal on a carbon support, a tertiary phosphine such as triphenylphosphine and a copper-based catalyst such as cuprous iodide.

The preparation of a compound of formula I also comprises reacting a compound of formula I wherein R is hydrogen with a compound of the formula Ar Hal in which Ar is an optionally substituted aryl or heteroaryl and Hal is halogen to obtain the corresponding compound of claim wherein R is aryl or heteroaryl.

The compounds of formula II are novel compounds and may be prepared by reacting a compound of the formula

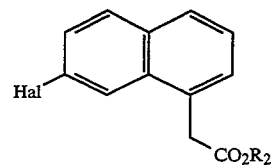  IV with a strong base and an alkyl formate.

The compounds of formula IV are described in French Patent Application 91 12516 filed on Oct. 11, 1991 and an example of the preparation of the compound formula IV is given in the examples.

The preparation of the compounds of formula IV can be schematized as follows:

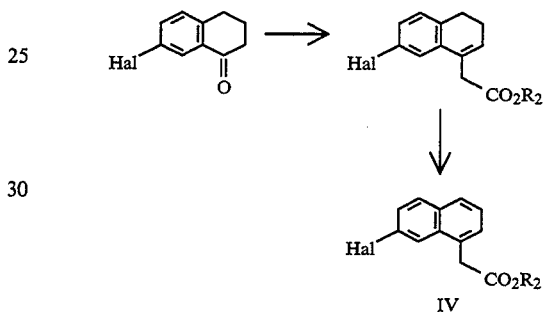

The compounds of formula I in which R is

are biologically-active products and can also serve as intermediates for the preparation of other biologically-active products by the following reaction diagrams:

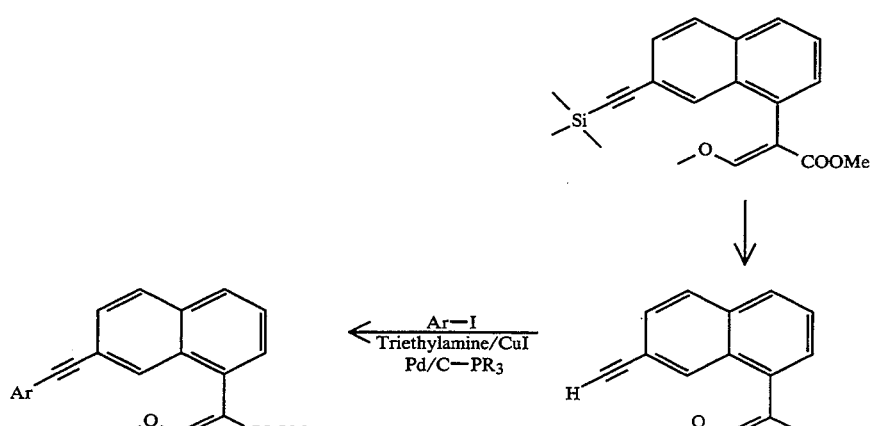

Ar: Aromatic or heteroaromatic

-continued

X: halogen

The compounds of formula I, in which R is hydroxyl can be functionalized with an alkylating reagent such as methyl iodide or dimethylsulfate to obtain the corresponding methyl derivatives. They can also be subjected to the action of D.A.S.T. (dimethyl amino sulfide trifluoride) to obtain derivatives in which R has at least one fluorine.

In the following examples, there are described several preferred embodiments to illustrate the invention. It is to be understood that the invention is not intended to be limited to the specific embodiments.

EXAMPLE 1 methyl (E) 7-(3,3-dimethyl 1-butynyl) α-(methoxy methylene) 1-naphthalene acetate 1.5 g of the product of Preparation 1 were introduced into an anhydrous mixture of 15 ml of triethylamine and 10 ml of acetonitrile and 0.198 g of 10% palladium on activated charcoal, 0.035 g of copper iodide, 0.195 g of triphenylphosphine and 0.60 ml of terbutylacetylene were added. The suspension was refluxed for 5 hours, 1 ml of terbutylacetylene was added and the reaction mixture was refluxed again for 2 hours. After filtering and evaporation to dryness, 2.62 g of a product were obtained which was chromatographed on silica eluting with a hexane-methylene chloride mixture (50—50). The fraction of Rf=0.20 was isolated, concentrated in a rotary evaporator, rinsed and dried at 50° C. to obtain 0.99 g of a product which was crystallized from ethyl acetate to obtain 0.630 g of the desired product melting at 172° C. δ (CDCl$_3$)=7.79 ppm.

Using the procedure of Example 1, the following products were obtained starting from the same product of formula II and the corresponding RC≡CH product.

Melting points are expressed in degrees Celsius and are determined using a METTLER PF62 apparatus.

Chemical displacements (δ) are expressed in ppm from a tetramethylsilane internal reference and are determined using a BRUCKER Nuclear Magnetic Resonance apparatus at 250 MHz.

EXAMPLE 2 methyl (E) α-(methoxymethylene) 7-[2-(trimethylsilyl)ethynyl] 1-naphthalene acetate melting at 157° C. δ (CDCl$_3$)=7.79 ppm.

EXAMPLE 3 methyl (E) 7-(1-hexynyl) δ -(methoxymethylene) 1-naphthalene acetate melting at 88° C. δ (CDCl$_3$)=7.78 ppm.

EXAMPLE 4 methyl (E) 7-[2-[1-(4-ethoxyphenyl)cyclopropyl]ethynyl]] α-(methoxymethylene) 1-naphthalene acetate melting at 145° C. δ (CDCl$_3$)=7.78 ppm.

EXAMPLE 5 methyl (E) α-(methoxymethylene) 7-(phenylethenyl) 1-naphthalene acetate melting at 161° C. δ (CDCl$_3$)=7.81 ppm.

EXAMPLE 6 methyl (E) 7-(3-hydroxy 3-methyl 1-butynyl) α-(methoxymethylene) 1-naphthalene acetate melting at 117° C. δ (CDCl$_3$)=7.80 ppm.

EXAMPLE 7 methyl (E) 7-(3-methoxy 3-methyl 1-butynyl) α-(methoxymethylene) 1-naphthalene acetate melting at 134° C. δ (CDCl$_3$)=7.80 ppm.

EXAMPLE 8 methyl (E) 7-(3-hydroxy 3-phenyl 1-propynyl) α-(methoxymethylene) 1-naphthalene acetate melting at 192° C. δ (CDCl$_3$)=7.78 ppm.

EXAMPLE 9 methyl (E) 7-(3-hydroxy 3-phenyl 1-butynyl)α-(methoxymethylene) 1-naphthalene acetate melting at 169° C. δ (CDCl$_3$)=7.79 ppm.

EXAMPLE 10 methyl (E) 7-(3-methyl 1-butynyl) α-(methoxymethylene) 1-naphthalene acetate melting at 114° C. δ (CDCl$_3$)=7.78 ppm.

EXAMPLE 11 methyl (E) α-(methoxymethylene) 7-(cyclopentyl ethynyl) 1-naphthalene acetate melting at 80° C. δ (CDCl$_3$)=7.78 ppm.

EXAMPLE 12 methyl (E) 7-(3-fluoro 3-methyl 1-butynyl) α-(methoxymethylene) 1-naphthalene acetate By reacting the product of Example 6 with the DAST (dimethyl amino sulfide trifluoride) at −10° C. in tetrahydrofuran, the desired product was obtained melting at 74° C. δ (CDCl$_3$)=7.80 ppm.

EXAMPLE 13 methyl (E) α-(methoxymethylene) 7-(ethynyl) 1-naphthalene acetate 18.1 ml of a 1N solution of Bu₄NF in THF were added at −50° C. to a solution of 6.15 g of methyl (E) α-(methoxymethylene) 7-[2-(trimethylsilyl)ethynyl] 1-naphthalene acetate (prepared in Example 2) and 180 ml of THF. The reaction mixture was stirred for 2 hours and was poured into an aqueous solution of potassium dihydrogen-phosphate, followed by extraction with methylene chloride, drying, evaporating the solvent to obtain 6.1 g of a product which was chromatographed on silica eluting with a hexane-ethyl acetate mixture (9-1) to obtain 4.2 g of the desired product melting at 140° C. δ (CDCl₃)=7.78 ppm.

EXAMPLE 14 methyl (E) α-(methoxymethylene) 7-(bromoethynyl) 1-naphthalene acetate 3.5 g of triphenylphosphine were added at 20° C. to a solution of 0.6 g of the product of Example 13, 2.24 g of carbon tetrabromide and 6 ml of methylene chloride and the reaction mixture was stirred for 15 minutes. It was poured into water, extracted with methylene chloride, dried and evaporated to obtain 6.2 g of a product which was taken up in a mixture of 20 ml of methylene chloride and 10 ml of ethyl ether. The precipitate was filtered and the filtrate was concentrated to obtain 2.1 g of a product which was chromatographed on silica eluting with a hexane-ethyl acetate mixture (8-2) to obtain 0.31 g of the desired product in the form of an oil. δ (CDCl₃)=7.78 ppm.

EXAMPLE 15 methyl (E) 7-[2-(4-chlorophenyl)ethynyl] α-(methoxymethylene) naphthalene acetate 0.15 g of 10% palladium on activated charcoal, 0.13 g of triphenylphosphine and 0.03 g of cuprous iodide were added to a solution of 1 g of the product of Example 13 and 1 g of bromo 4-chlorobenzene in 10 ml of triethylamine and 6 ml of anhydrous acetonitrile. The suspension was refluxed under a nitrogen atmosphere for 2 hours 30 minutes and then was filtered. The filtrate was diluted with methylene chloride and washed with a 2N aqueous solution of hydrochloric acid, dried over MgSO₄ then evaporated under reduced pressure. The residue was chromatographed on silica (eluant: CH₂Cl₂-hexane 7-3) to obtain 0.75 g of the desired product melting at 162° C.

EXAMPLE 16 methyl (E) 7-[2-(4-bromophenyl)ethynyl] α-(methoxymethylene) naphthalene acetate A solution of 20 ml of dimethylformamide containing 1.5 g of the product of Example 13, 1.6 g of iodo 4-bromobenzene, 0.025 g of palladium dichloro bis(triphenylphosphine), 0.023 g of cuprous iodide and 1. ml of triethylamine was stirred at 20° C., under a nitrogen atmosphere for 6 hours and was then poured into water and extracted with diisopropyl ether. The organic phase was dried over MgSO₄ and evaporated under reduced pressure. The residue was chromatographed on silica (eluant: CH₂Cl₂-hexane 8-2) to obtain 2.03 g of the desired product melting at 173° C.

Using the above procedure, the following products were prepared:

EXAMPLE 17 methyl (E) α-(methoxymethylene) 7-[3-methyl 3-phenyl 1-butynyl] naphthalene acetate melting at 136° C.

EXAMPLE 18 methyl (E) 7-[2-(3-chlorophenyl)ethynyl] α-(methoxymethylene) naphthalene acetate melting at 194° C.

EXAMPLE 19 methyl (E) α-(methoxymethylene) 7-[2-(4-pyridinyl)ethynhl] naphthalene acetate melting at 194° C.

EXAMPLE 20 methyl (E) α-(methoxymethylene) 7-[2-(4-phenoxyphenyl)ethynyl] naphthalene acetate melting at 182° C.

EXAMPLE 21 methyl (E) 7-[3-[(2-methoxy)ethoxy]methoxy 1-propynyl] α-(methoxymethylene) naphthalene acetate melting at 76° C.

EXAMPLE 22 methyl (E) 7-[2-(2-chlorophenyl)ethynyl] α(methoxymethylene) naphthalene acetate melting at 146° C.

EXAMPLE 23 methyl (E) α-(methoxymethylene) 7-[3-methyl 3-(1-piperidinyl) 1-butynyl] naphthalene acetate melting at 145° C.

EXAMPLE 24 methyl (E) α-(methoxymethylene) 7 -[2-(3-pyridinyl)ethynyl] naphthalene acetate melting at 142° C.

EXAMPLE 25 methyl (E) α-(methoxymethylene) 7 -[2-(2-pyridinyl)ethynyl] naphthalene acetate melting at 148° C.

EXAMPLE 26 methyl (E) α-(methoxymethylene) 7 -[3-(4-methylphenoxy) 3-methyl 1-butynyl] naphthalene acetate M.p.<50° C.

EXAMPLE 27 methyl (E) α-(methoxymethylene) 7-[3-methyl 3-(methylpropylamino) 1-butynyl] naphthalene acetate melting at 128° C.

EXAMPLE 28 methyl (E) 7-[3-(4-chlorophenoxy) 3-methyl 1-butynyl] α-(methoxymethylene) naphthalene acetate melting at 114° C.

EXAMPLE 29 methyl (E) 7 -[2-(3-bromophenyl)ethynyl] α-(methoxymethylene) naphthalene acetate melting at 204° C.

EXAMPLE 30 methyl (E) α-(methoxymethylene) 7-[3-methyl 3-(methylamino) 1-butynyl] naphthalene acetate melting at 152° C.

EXAMPLE 37 methyl (E) 7-[2-[3-(4-fluorophenyl)phenyl]ethynyl] α-(methoxymethylene) naphthalene acetate melting at 164° C.

EXAMPLE 32 methyl (E) 7-[3,3-dimethyl 1-butynyl] α-[[1-(methyl)ethoxy]methylene] naphthalene acetate melting at 111° C.

EXAMPLE 33 methyl (E) α-(ethoxymethylene) 7-[3,3-dimethyl 1-butynyl] naphthalene acetate melting at 98° C.

EXAMPLE 34 methyl (E) α-(methoxymethylene) 7-[3-methyl 3-(phenylamino) 1-butynyl] naphthalene acetate melting at 154° C.

EXAMPLE 35 methyl (E) 7-[3-[[(2-methoxy)ethoxy]methoxy]3-methyl 1-butynyl] α-(methoxymethylene) naphthalene acetate melting at 670° C.

EXAMPLE 36 methyl (E) 7-[3,3-dimethyl 1-butynyl] α-(methoxymethylene) naphthalene acetate of 2-trimethylsilyl) ethyl melting at 105° C.

EXAMPLE 37 methyl (E) 7-[2-(4-fluorophenyl)ethynyl] α-(methoxymethylene) naphthalene acetate melting at 170° C.

EXAMPLE 38 methyl (E) 7-[2-(4-methoxyphenyl)ethynyl] α-(methoxymethylene) naphthalene acetate melting at 164° C.

EXAMPLE 39 methyl (E) α-(methoxymethylene) 7-[3-(trimethylsilyl) 1-propynyl] naphthalene acetate melting at 107° C.

EXAMPLE 40 methyl (E) 7-[3-(4-chlorophenyl) 3-methyl 1-butynyl] α-(methoxymethylene) naphthalene acetate melting at 152° C.

EXAMPLE 41 methyl (E) 7-[2-(3,4-dichlorophenyl) ethynyl] α-(methoxymethylene) naphthalene acetate melting at 200° C.

EXAMPLE 42 methyl (E) 7-[3-(4-chlorophenyl)amino]3-methyl 1-butynyl] α-(methoxymethylene) naphthalene acetate melting at 149° C.

EXAMPLE 43 methyl (E) α-(methoxymethylene) 7-[3-[methyl(phenylamino) 3-methyl]1-butynyl] naphthalene acetate melting at 158° C.

EXAMPLE 44 methyl (E) 7-[2-[4-(1,1-dimethylethyl)phenyl]ethynyl] α-(methoxymethylene) naphthalene acetate melting at 182° C.

EXAMPLE 45 methyl (E) α-((methoxymethylene) 7-[2-(4-methylphenyl)ethynyl] naphthalene acetate melting at 164° C.

EXAMPLE 46 methyl (E) 7-[2-(4-bromo 2-fluorophenyl)ethynyl] α(methoxymethylene) naphthalene acetate melting at 135° C.

EXAMPLE 47 methyl (E) 7-[2-(3-chloro 4-fluorophenyl)ethynyl] α(methoxymethylene) naphthalene acetate melting at 210° C.

EXAMPLE 48 methyl (E) 7-[2-(3,5-dichlorophenyl)ethynyl] α-methoxy methylene) naphthalene acetate melting at 180° C.

EXAMPLE 49 methyl (E) α-(methoxymethylene) 7-[2-[4-(trifluoromethoxy)phenyl]ethynyl] naphthalene acetate melting at 150° C.

EXAMPLE 50 methyl (E) 7-(3,3-dimethylbutynyl] α-methoxy methylene) naphthalene acetate melting at 138° C.

EXAMPLE 51 methyl (E) α-(methoxymethylene) 7-[2-[4-(trifluoromethyl)phenyl]ethynyl] naphthalene acetate melting at 157° C.

EXAMPLE 52 methyl (E)
7-[2-(3,5-bis(trifluoromethyl)phenyl]ethynyl]
α-(methoxymethylene) naphthalene acetate melting at 192° C.

EXAMPLE 53 methyl (E) 7-[2-(1,3-benzodioxol-5-yl)ethynyl]
α-(methoxymethylene) naphthalene acetate melting at 181° C.

EXAMPLE 54 methyl (E) 7-[3-(dimethylamino) 3-methyl 1-butynyl]
α-(methoxymethylene) naphthalene acetate melting at 148° C.

EXAMPLE 55 methyl (E) 7-(1-propynyl) α-(methoxy-methylene)
naphthalene acetate melting at 109° C.

EXAMPLE 56 methyl (E) 7-[3-[(4-chlorophenyl)methylamino]
3-methyl 1-butynyl] α-(methoxymethylene)
naphthalene acetate melting at 179° C.

EXAMPLE 57 methyl (E) 7-[2-(4-cyanophenyl)ethynyl]
α-(methoxymethylene) naphthalene acetate melting at 129° C.

EXAMPLE 58 methyl (E) 7-[2-(2,4-dichlorophenyl)ethynyl]
α-methoxy methylene) naphthalene acetate melting at 156° C.

EXAMPLE 59 methyl (E) 7-[2-(2,3-dichlorophenyl)ethynyl]
α-methoxy methylene) naphthalene acetate melting at 153° C.

EXAMPLE 60 methyl (E) 7-[2-(2,5-dichlorophenyl)ethynyl]
α-(methoxymethylene) naphthalene acetate melting at 162° C.

EXAMPLE 61 methyl (E) 7-[3-(1,1-dimethylethoxy) 3-methyl
1-butynyl] α-(methoxymethylene) naphthalene acetate melting at 140° C.

PREPARATION 1 methyl 1-(E) 7-bromo (α-methoxy methylene)
1-naphthalene acetate

A solution of 5.99 g of the product of Preparation 2, 70 ml of DMF and 28.5 ml of methyl formate was added to a solution of 2.02 g of sodium hydride and 20 ml of anhydrous DMF. The reaction mixture was stirred for 35 minutes and was poured into an aqueous solution of hydrochloric acid and extracted with ether. The extracts were dried, filtered and evaporated to obtain 9.54 g of a product which was taken up in 60 ml of acetone. 8.70 g of potassium carbonate and 2.4 ml of dimethyl sulfate were added. The reaction mixture was stirred at 20° C. for 16 hours and then was poured into water. Separation was carried out and the product was rinsed to obtain 8.67 g of a product which was chromatographed on silica eluting with a hexane-methylene chloride-acetone mixture (90-5-5) to obtain 5.08 g of the expected product melting at 149° C.

PREPARATION 2 methyl 7-bromo 1-naphthalene acetate

STAGE A: methyl 7-bromo 3,4-dihydro 1-naphthalene acetate

A suspension of 5.8 g of activated zinc powder (i.e. obtained after washings with 20% hydrochloric acid by volume then with 5% hydrochloric acid, then with water, then with ethanol and finally with ethyl ether and drying), 70 ml of anhydrous tetrahydrofuran, 1 crystal of iodine and 0.1 ml of methyl bromoacetate was heated at 60° C. and a solution of 10 g of 7-bromotetralone [prepared by J. Org. Chem., Vol. 27, p. 76 (1962)], 5 ml of methyl bromoacetate and 60 ml of anhydrous tetrahydrofuran was added under a nitrogen atmosphere. The reaction medium was stirred at 20° C. for 2 hours, poured into water, neutralized by the addition of ammonium chloride and extracted with ether. The aqueous solution was filtered and reextracted with ether. The combined organic phases were washed with a saturated aqueous solution of sodium chloride, dried and evaporated under reduced pressure to obtain 13.6 g of a product which was dissolved in 90 ml of trifluoroacetic acid. Heating took place at 50° C. for 30 minutes and the mixture was poured into a solution of 1 liter of water and 500 ml of ether. Potassium carbonate was added until a pH close to 10 was reached. After decanting, washing with a saturated aqueous solution of sodium chloride, drying and evaporating under reduced pressure, 11.8 g of product were obtained which was chromatographed on silica eluting with a hexane-isopropyl ether mixture (9-1), then with a hexane-isopropyl ether mixture (7-3) to obtain 9.9 g of the desired product.

TLC (silica) eluant: hexane-isopropyl ether (8-2)
Rf=0.38.

| NMR Spectrum (250 MHz) | |
| --- | --- |
| $CH_2$ in position 3 | approx. 2.32 (m) |
| $CH_2$ in position 4 | 2.73 (t) |
| =C—$CH_2$—C=O | 3.41 (s) |
| $CO_2CH_3$ | 3.71 (s) |
| $H_2$ | 6.04 (t) |
| $H_5$ | 7.00 (d) |
| $H_8 + H_6$ | approx. 7.25 (m) |

STAGE B: methyl 7-bromo 1-naphthalene acetate

A solution of 9.85 g of the product of Stage A was heated at 90° C. for 3 hours 30 minutes with 10.3 g of dichlorodicyanobenzoquinone and 300 ml of toluene. The reaction mixture was stirred at 20° C. for 12 hours and after filtering and evaporating under reduced pressure, 12.7 g of product were obtained which was chromatographed on silica, eluting with a hexane-methylene chloride mixture (7-3) to obtain 5.1 g of the desired product melting at 61° C.

| NMR Spectrum (250 MHz) | |
|---|---|
| COOCH$_3$ | 3.66 (s) |
| =C$_6$H$_3$—CH$_2$—CO | 3.98 (s) |
| H$_8$ | 8.1 (sl) |
| | 7.42 (m) |
| Aromatic H's | 7.52 (dd) 1H |
| | 7.68 (m) 2H |

A) Study of the activity on *Aphis craccivora*

Bean plants were treated by soaking the leaves in a water-acetone solution of active ingredient (50% acetone, 50% water), then dried under an extraction hood. The leaves were then infested: 20 adult females of *Aphis craccivora* per leaf and maintained at 22° C. under an illuminated ceiling. Mortality checks were carried out after 48 hours.

C) Study of the acaricide activity on Tetranychus Urticae

Haricot plants with two leaves were used and they were infested with 30 *Tetranychus urticae* females per leaf and were placed under an aerated hood with a lighted ceiling with continuous illumination. The plants were treated with a Fisher gun: 4 ml of toxic solution of a mixture of equal volumes of water and acetone per plant. After drying for 30 minutes, infestation was proceeded with and the mortality checks were carried out after 3 days.

C) Study of the effect on larvae of *Spodoptera littoralis* by contact and ingestion.

L3 stage larvae of Spodoptera Littoralis were used and the operation was carried out at 22° C. in relative humidity conditions of 50%. PETRI dishes were used containing a circle of damp filter paper and two bean leaves treated with a water-acetone solution (50-50) of the product to be tested were placed in each dish. The number of dead larvae after 7 days is counted.

D) Study of the effect on *Phaedon cochleariae*.

The operation was carried out at 22° C. in relative humidity conditions of 50%. PETRI dishes were used containing a circle of damp filter paper and two disks of Chinese cabbage leaf treated with a water-acetone solution (50-50) of the product to be tested were used. The number of dead insects after one week was counted.

Results

Starting from a dose of 100 ppm, the products of the invention showed a useful insecticide activity.

Various modifications of the compounds and method of the invention may be made without departing from the spirit or scope thereof and it is to be understood that the invention is intended to be limited only as defined in the appended claims.

What we claim is:

1. A compound of the formula

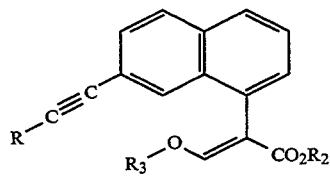

I wherein R is selected from the group consisting of A) halogen and hydrogen, B) alkyl, alkenyl, alkynyl and cycloalkyl of up to 8 carbon atoms optionally substituted with at least one member of the group consisting of hydroxy and halogen and optionally interrupted by at least one heteroatom selected from the group consisting of —O—, —S— and nitrogen, C)

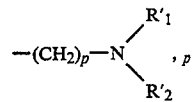

is an integer from 0 to 6, R'$_1$ and R'$_2$ are individually hydrogen or alkyl of 1 to 4 carbon atoms, D) aryl and aryloxy of up to 18 carbon atoms optionally substituted on the aryl by at least one member of the group consisting of halogen, —NO$_2$, —CN, optionally unsaturated alkoxy, alkylthio and cycloalkyl of up to 8 carbon atoms optionally substituted by at least one halogen, aryl and aryloxy of up to 16 carbon atoms optionally substituted by at least one halogen and

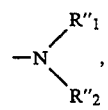

R"$_1$ and R"$_2$ are individually selected from the group consisting of hydrogen, alkyl of 1 to 4 carbon atoms and aryl of up to 18 carbon atoms optionally substituted with at least one halogen, E) aryl and aryloxy of up to 18 carbon atoms optionally substituted on 2 adjacent carbon atoms of the aryl nucleus with methylenedioxy or ethylenedioxy optionally substituted with 1 or 2 halogen atoms, F) heterocyclic aryl of 5 to 6 ring members containing 1 to 3 heteroatoms selected from the group consisting of —O—, —S— and nitrogen and optionally substituted with at least one member of the group consisting of —OH, —NO$_2$, —CN, halogen, alkyl, alkoxy, alkylthio and cycloalkyl of up to 8 carbon atoms optionally substituted by at least halogen and/or hydroxy and

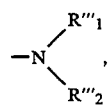

R'''$_1$ and R'''$_2$ are individually hydrogen or alkyl of 1 to 4 carbon atoms, G)

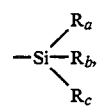

R$_a$, R$_b$ and R$_c$ are individually selected from the group consisting of alkyl and cycloalkyl of up to 4 carbon atoms optionally substituted by at least one halogen, aryl optionally substituted by at least one member of the group consisting of halogen, —OH and alkyl, alkoxy and alkylthio optionally substituted with at least one halogen and H)

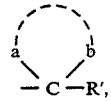

a and b are individually selected from the group consisting of hydrogen, halogen, —OH, alkyl of 1 to 6 carbon atoms optionally substituted by at least one halogen and alkoxy of 1 to 6 carbon atoms or a and b together with the carbon to which they are attached form cycloalkyl of up to 6 carbon atoms, R' has the value of R and $R_2$ and $R_3$ are individually selected from the group consisting alkyl and cycloalkyl of up to 8 carbon atoms optionally substituted by at least one halogen and

wherein $R_a$, $R_b$ and $R_c$ have the above definitions.

2. A compound of claim 1 wherein $R_2$ is methyl compound of claim 1 wherein $R_3$ is methyl.

3. A compound of claim 1 wherein $R_3$ is methyl.

4. A compound of claim 1 wherein the geometry of the exo (enol ether) double bond is E.

5. A compound of claim 1 wherein R is alkyl of 1 to 6 carbon atoms.

6. A compound of claim 1 wherein R is n-butyl or terbutyl radical.

7. A compound of claim 1 wherein R is

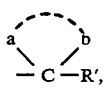

a and b are individually hydrogen, —OH or alkyl of 1 to 4 carbon atoms or a and b together with the carbon atom to which they are attached form cycloalkyl of up to 6 carbon atoms.

8. A compound of claim 1 wherein a and b are identical and are hydrogen or methyl or form with the carbon atom to which they are attached cyclopropyl.

9. A compound of claim 1 wherein R or R' is

and Ra, Rb and Rc are individually alkyl of 1 to 4 carbon atoms.

10. A compound of claim 9, wherein Ra, Rb and Rc are methyl.

11. A compound of claim 1 wherein R or R' are phenyl optionally substituted with at least one member of the group consisting of halogen, —OH, alkyl and alkoxy of 1 to 4 carbon atoms, methylenedioxy, ethylenedioxy and $CF_3$.

12. A compound of claim 11 wherein the phenyl is optionally substituted with at least one member of the group consisting of chlorine, bromine, —$CF_3$, ethoxy and methylenedioxy.

13. A compound of claim 1 selected from the group consisting of
methyl (E) 7-(3,3-dimethyl 1-butynyl)-α-(methoxymethylene) 1-naphthalene acetate,
methyl (E) α-(methoxymethylene)-7-[2-(trimethylsilyl)ethynyl]1-naphthalene acetate,
methyl (E) 7-(1-hexynyl)-α-(methoxymethylene) 1-naphthalene acetate,
methyl (E) 7-[2-[1-(4-ethoxy phenyl)-cyclopropyl]-ethynyl]α-(methoxymethylene)-1-naphthalene acetate,
methyl (E) 7-[2-(4-chlorophenyl)-ethynyl]-α-(methoxymethylene) naphthalene acetate,
methyl (E) 7-[2-(4-bromophenyl)-ethynyl]-α-(methoxymethylene) naphthalene acetate,
methyl (E) α-(methoxymethylene)-7-[3-methyl-3-phenyl 1-butynyl]naphthalene acetate,
methyl (E) 7-[2-(3-bromophenyl)-ethynyl]α-(methoxy-methylene)naphthalene acetate,
methyl (E) α-(methoxymethylene)-7-[3-(trimethylsilyl)1-propynyl]naphthalene acetate,
methyl (E) 7-[3-(4-chlorophenyl)-3-methyl1-butynyl-]α-(methoxymethylene)-naphthalene acetate,
methyl (E) α-(methoxymethylene)-7-[2-[4-trifluoromethyl phenyl]ethynyl]naphthalene acetate and
methyl (E) 7-[2-(3,5-bis(trifluoromethyl)-phenyl]-ethynyl]-α-(methoxymethylene)-naphthalene acetate,
methyl (E) 7-[2-(1,3-benzodioxol-5-yl)-ethynyl]-α-(methoxymethylene) naphthalene acetate.

14. An insecticidal composition comprising an insecticidally effective amount of at least one compound of claim 1 and an inert carrier.

15. An acaricide composition comprising an acaricidally effective amount of at least one compound of claim 1 and an inert carrier.

16. A nematocidal composition comprising a nematocidally effective amount of at least one compound of claim 1 and an inert carrier.

17. A method of combatting parasites of warm-blooded animals comprising contacting warm-blooded animals with a parasitically effective amount of at least one compound of claim 1.

18. A method of combatting insects comprising contacting insects with an insecticidally effective amount of at least one compound of claim 1.

19. A method of combatting nematodes comprising contacting nematodes with a nematocidally effective amount of at least one compound of claim 1.

* * * * *